US 7,884,213 B2
Feb. 8, 2011

(12) United States Patent
Gaitonde et al.

(10) Patent No.: US 7,884,213 B2
(45) Date of Patent: Feb. 8, 2011

(54) PROCESS FOR THE PREPARATION OF ANASTROZOLE

(75) Inventors: Abhay Gaitonde, Maharashtra (IN); Chitra Vaidya, Maharashtra (IN); Sanjay R. Pawar, Maharashtra (IN)

(73) Assignee: Generics [UK] Limited, Hertfordshire (GB)

( * ) Notice: Subject to any disclaimer, the term of this patent is extended or adjusted under 35 U.S.C. 154(b) by 820 days.

(21) Appl. No.: 11/630,421

(22) PCT Filed: Jun. 22, 2005

(86) PCT No.: PCT/GB2005/050096

§ 371 (c)(1), (2), (4) Date: Sep. 10, 2007

(87) PCT Pub. No.: WO2006/000836

PCT Pub. Date: Jan. 5, 2006

(65) Prior Publication Data

US 2008/0096946 A1    Apr. 24, 2008

(30) Foreign Application Priority Data

Jun. 24, 2004 (GB) .................. 0414120.6

(51) Int. Cl.
*C07D 249/08* (2006.01)
*A61K 31/4196* (2006.01)

(52) U.S. Cl. .................. 548/267.4; 548/262.2

(58) Field of Classification Search ............ None
See application file for complete search history.

(56) References Cited

U.S. PATENT DOCUMENTS 4,935,437 A * 6/1990 Edwards et al. ............ 514/383

FOREIGN PATENT DOCUMENTS

EP    0 296 749 A1    12/1988

* cited by examiner

*Primary Examiner*—Fiona T Powers
(74) *Attorney, Agent, or Firm*—Wolf, Greenfield & Sacks, P.C.

(57) ABSTRACT

A process for the preparation of anastrozole.

28 Claims, 2 Drawing Sheets a: MeI, NaH
b: CrO₃, acetic anhydride, H₂SO₄
c: H₂N-NHBoc
d: HCO₂NH₄, Pd/C
e: HCl
f: s-triazine

PROCESS FOR THE PREPARATION OF ANASTROZOLE

RELATED APPLICATIONS

This application is a national stage filing under 35 U.S.C. §371 of international application PCT/GB2005/050096, filed Jun. 22, 2005, which was published under PCT Article 21(2) in English.

TECHNICAL FIELD

The present invention relates to a novel process for the preparation of anastrozole, comprising two or more of the steps specified in FIG. 1. The present invention also relates to novel intermediates used in the process of the present invention, such as hydrazone 4a, hydrazine 5a, hydrazine salt 6a and aldehyde 3.

The present invention further relates to anastrozole or a pharmaceutically acceptable salt or derivative thereof, when prepared by a process according to the present invention, and the use of the anastrozole or the pharmaceutically acceptable salt or derivative thereof in the treatment of breast cancer.

BACKGROUND ART

The present invention relates to a novel process for the preparation of 2,2'-[5-(1H-1,2,4-triazol-1-ylmethyl)-1,3-phenylene]di(2-methylpropionitrile), which is more commonly known by its generic name, anastrozole.

Anastrozole is a non-steroidal aromatase inhibitor which is marketed for the treatment of advanced breast cancer.

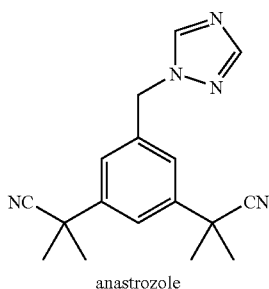

anastrozole

A process for the preparation of anastrozole is disclosed in patent EP 0296749 B1. However, there is always a need to have alternative processes for the manufacture of commercially valuable pharmaceuticals.

The inventors have therefore developed a novel process for the preparation of anastrozole. The novel process involves the use of novel intermediates and affords anastrozole in high yield and high purity.

SUMMARY OF THE INVENTION

A first aspect of the present invention provides a process for the preparation of anastrozole, comprising two or more of the steps specified in FIG. 1, wherein R represents a protecting group for the hydrazine and hydrazone moieties, and X represents an acid addition salt of the hydrazine.

The first aspect of the present invention therefore provides a process for the preparation of anastrozole, comprising two or more of the steps:

(a) methylation of diacetonitrile 1 to yield diacetonitrile 2,

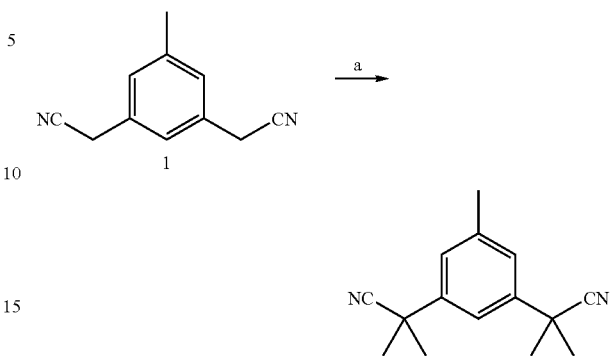

(b) oxidation of diacetonitrile 2 to yield aldehyde 3,

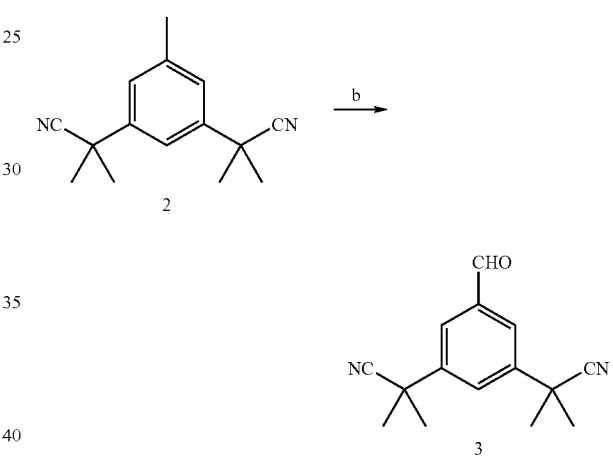

(c) conversion of aldehyde 3 to yield hydrazone 4a,

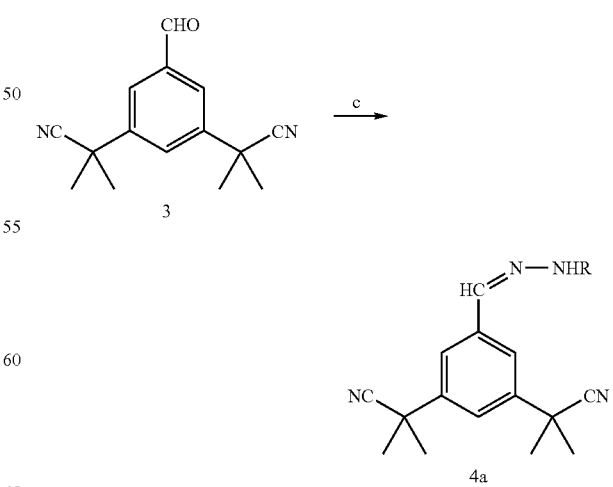

(d) reduction of hydrazone 4a to yield hydrazine 5a,

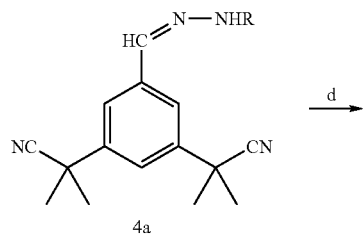

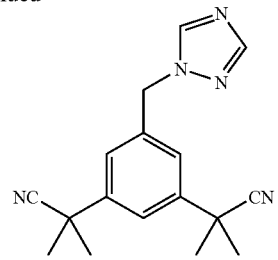

(e) conversion of hydrazine 5a to yield hydrazine salt 6a, and

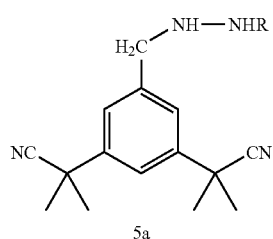

(f) conversion of hydrazine salt 6a to yield anastrozole

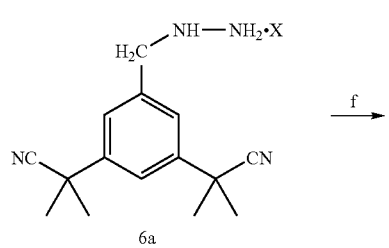

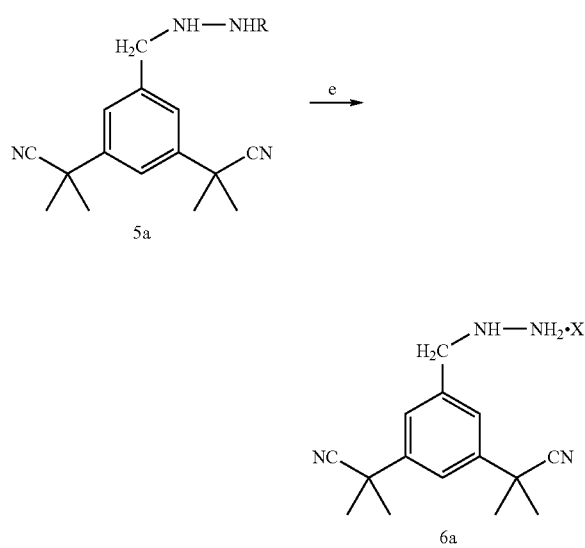

wherein R represents a protecting group for the hydrazine and hydrazone moieties, and X represents an acid addition salt of the hydrazine.

Preferably the process of the present invention comprises two, three, four, five or more of the process steps. More preferably the process of the present invention comprises all six of the process steps.

R is any suitable protecting group for the hydrazine and hydrazone moieties. Suitable protecting groups for protecting hydrazine and hydrazone moieties are known in the art, for example from "Protective Groups in Organic Synthesis" by T. W. Greene and P. G. M. Wuts (Wiley-Interscience, $2^{nd}$ edition, 1991). Preferably R is selected from an acyl group, an alkyl group, an alkyloxy group or an alkyloxycarbonyl group. Preferably R is an acid-labile protecting group. Preferably R is selected from an acetyl, benzoyl, benzyl, p-methoxybenzyl or t-butyloxycarbonyl (Boc) group; more preferably R represents a t-butyloxycarbonyl (Boc) group.

X represents any suitable acid addition salt of the hydrazine. Preferably X is selected from hydrochloric acid, hydrobromic acid, sulfuric acid, succinic acid, maleic acid, oxalic acid or a sulfonic acid; more preferably X represents hydrochloric acid (HCl).

In the most preferred embodiment of the present invention, R represents a t-butyloxycarbonyl (Boc) group, and X represents hydrochloric acid (HCl), which is represented by FIG. 2.

Preferably, in step (a), diacetonitrile 1 is methylated to yield diacetonitrile 2 using sodium hydride and iodomethane. Preferably, in step (b), diacetonitrile 2 is oxidised to yield aldehyde 3 using chromium trioxide, preferably chromium trioxide, acetic anhydride and sulfuric acid. Preferably, in step (c), aldehyde 3 is converted into hydrazone 4a using $H_2N$—NHR. Preferably, in step (d), hydrazone 4a is reduced to yield hydrazine 5a by hydrogenation, preferably using ammonium formate and a catalyst such as palladium on carbon paste. Preferably, in step (e), hydrazine 5a is deprotected using an acid and converted into hydrazine acid addition salt 6a using an acid; preferably the acid used for deprotection is the same as the acid used for forming the acid addition salt. Preferably, in step (f), hydrazine salt 6a is converted into anastrozole using s-triazine.

The process of the present invention affords anastrozole in high yield and high purity.

Preferably anastrozole is obtained in an overall yield of 14.5% or more from diacetonitrile 1. In step (a), diacetonitrile 2 is preferably obtained in a yield of 79% or more from diacetonitrile 1. In step (b), aldehyde 3 is preferably obtained in a yield of 78% or more (preferably 78.34% or more) from diacetonitrile 2. In step (c), hydrazone 4a is preferably obtained in a yield of 77% or more (preferably 77.21% or more) from aldehyde 3. In step (d), hydrazine 5a is preferably obtained in a yield of 80% or more from hydrazone 4a. In step (e), hydrazine salt 6a is preferably obtained in a yield of 52% or more (preferably 52.82% or more) from hydrazine 5a. In step (f), anastrozole is preferably obtained in a yield of 72% or more (preferably 72.49% or more) from hydrazine salt 6a.

Preferably the anastrozole obtained is more than 98%, 99%, 99.5%, 99.7% or 99.9% pure. Preferably purity is measured by HPLC.

The process of the present application is suitable for industrial scale manufacture of anastrozole. Preferably anastrozole is obtained in batches of 5.6 g or more. Preferably anastrozole is obtained on an industrial scale, such as in batches of 0.5 kg, 1 kg, 5 kg, 10 kg, 25 kg or more.

A second aspect of the present invention provides anastrozole or a pharmaceutically acceptable salt or derivative thereof, when prepared by a process according to the first aspect of the present invention. Preferably the anastrozole or the pharmaceutically acceptable salt or derivative thereof is more than 98%, 99%, 99.5%, 99.7% or 99.9% pure. Preferably the anastrozole or the pharmaceutically acceptable salt or derivative thereof is suitable for use as a medicament. Preferably the medicament is suitable for the treatment of breast cancer.

A third aspect of the present invention provides a hydrazone of formula 4a

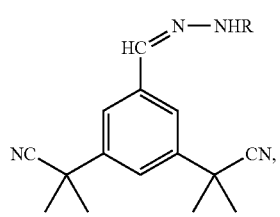

4a wherein R represents a protecting group. R is any suitable protecting group for the hydrazine and hydrazone moieties. Suitable protecting groups for protecting hydrazine and hydrazone moieties are known in the art, for example from "Protective Groups in Organic Synthesis" by T. W. Greene and P. G. M. Wuts (Wiley-Interscience, $2^{nd}$ edition, 1991). Preferably R is selected from an acyl group, an alkyl group, an alkyloxy group or an alkyloxycarbonyl group. Preferably R is an acid-labile protecting group. Preferably R is selected from an acetyl, benzoyl, benzyl, p-methoxybenzyl or t-butyloxycarbonyl (Boc) group; more preferably R represents a t-butyloxycarbonyl (Boc) group.

A fourth aspect of the present invention provides a hydrazine of formula 5a

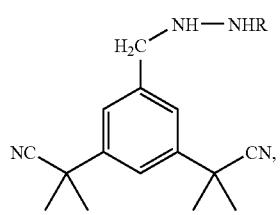

5a wherein R represents a protecting group. R is any suitable protecting group for the hydrazine and hydrazone moieties. Suitable protecting groups for protecting hydrazine and hydrazone moieties are known in the art, for example from "Protective Groups in Organic Synthesis" by T. W. Greene and P. G. M. Wuts (Wiley-Interscience, $2^{nd}$ edition, 1991). Preferably R is selected from an acyl group, an alkyl group, an alkyloxy group or an alkyloxycarbonyl group. Preferably R is an acid-labile protecting group. Preferably R is selected from an acetyl, benzoyl, benzyl, p-methoxybenzyl or t-butyloxycarbonyl (Boc) group; more preferably R represents a t-butyloxycarbonyl (Boc) group.

A fifth aspect of the present invention provides a hydrazine salt of formula 6a

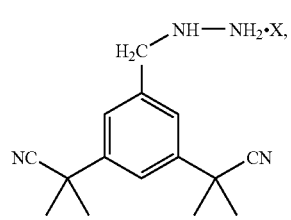

6a wherein X represents an acid addition salt of the hydrazine. X represents any suitable acid addition salt of the hydrazine. Preferably X is selected from hydrochloric acid, hydrobromic acid, sulfuric acid, succinic acid, maleic acid, oxalic acid or a sulfonic acid; more preferably X represents hydrochloric acid (HCl).

A sixth aspect of the present invention provides an aldehyde of formula 3

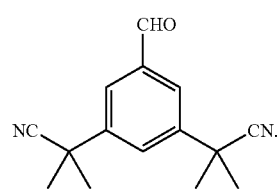

3

A seventh aspect of the present invention provides a pharmaceutical composition, comprising anastrozole or a pharmaceutically acceptable salt or derivative thereof according to the second aspect of the present invention, and a pharmaceutically acceptable carrier or diluent. Preferably the pharmaceutical composition is suitable for the treatment of breast cancer.

An eighth aspect of the present invention provides a use of anastrozole or a pharmaceutically acceptable salt or derivative thereof according to the second aspect of the present invention, for the manufacture of a medicament for the treatment of breast cancer.

A ninth aspect of the present invention provides a method of treating breast cancer, comprising administering to a subject in need of such treatment a therapeutically effective amount of anastrozole or a pharmaceutically acceptable salt or derivative thereof according to the second aspect of the present invention, or a therapeutically effective amount of a pharmaceutical composition according to the seventh aspect of the present invention.

BRIEF DESCRIPTION OF THE DRAWINGS

The present invention will now be described by way of example with reference to the accompanying drawings in which.

DETAILED DESCRIPTION OF THE INVENTION

Figure 1:
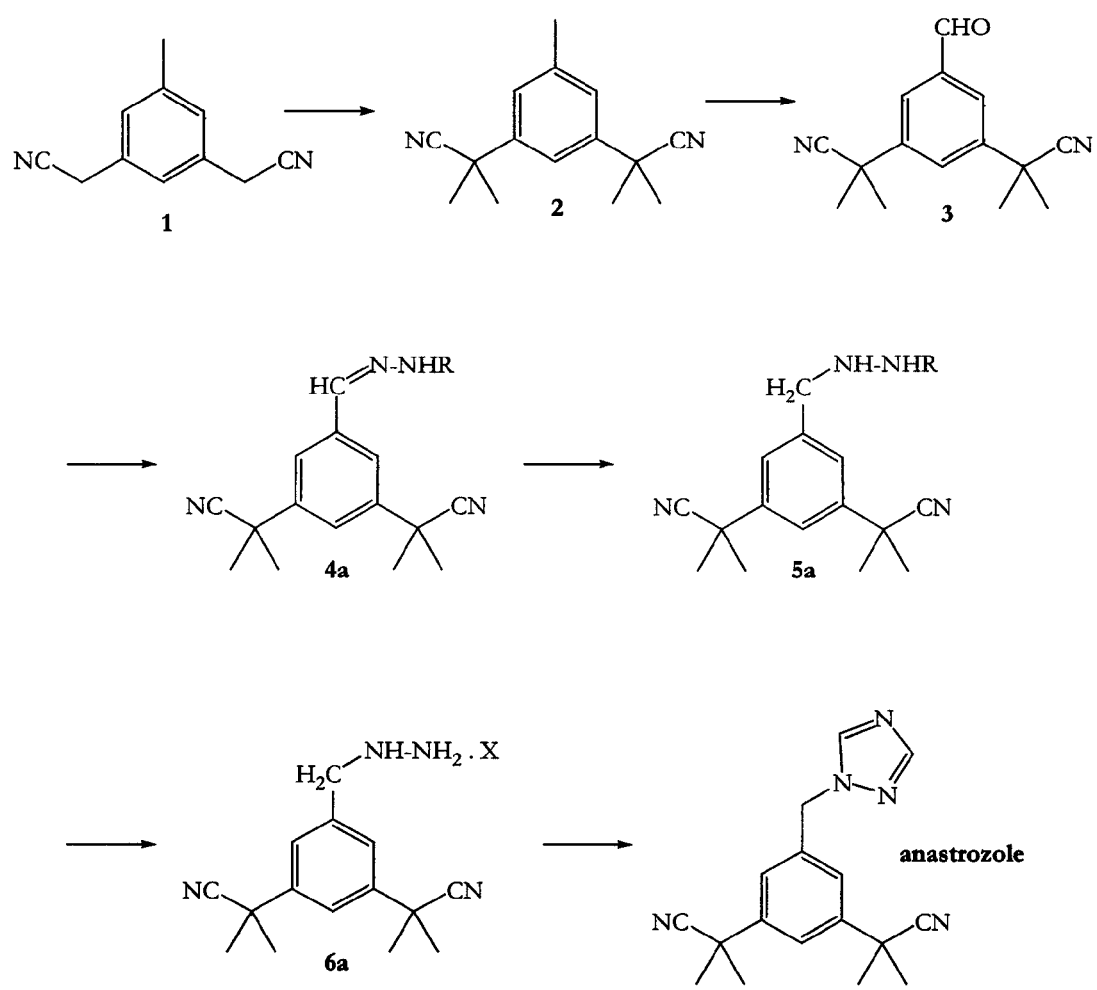
FIG. 1 is a schematic illustration of the process of the present invention.

The process of the invention is illustrated in FIG. 1. In this process, R represents a protecting group for the hydrazine and hydrazone moieties. R is typically an acyl group, an alkyl group, an alkyloxy group or an alkyloxycarbonyl group. Typical examples of such groups are acetyl, benzoyl, benzyl, p-methoxybenzyl and t-butyloxycarbonyl (Boc). The most preferred embodiment is when R represents Boc.

In FIG. 1, X represents an acid addition salt of the hydrazine. Typical examples of acids that could be used are hydrochloric acid, hydrobromic acid, sulfuric acid, succinic acid, maleic acid, oxalic acid or a sulfonic acid. A preferred embodiment of the first aspect of the invention is when X represents hydrochloric acid (HCl).

Figure 2:
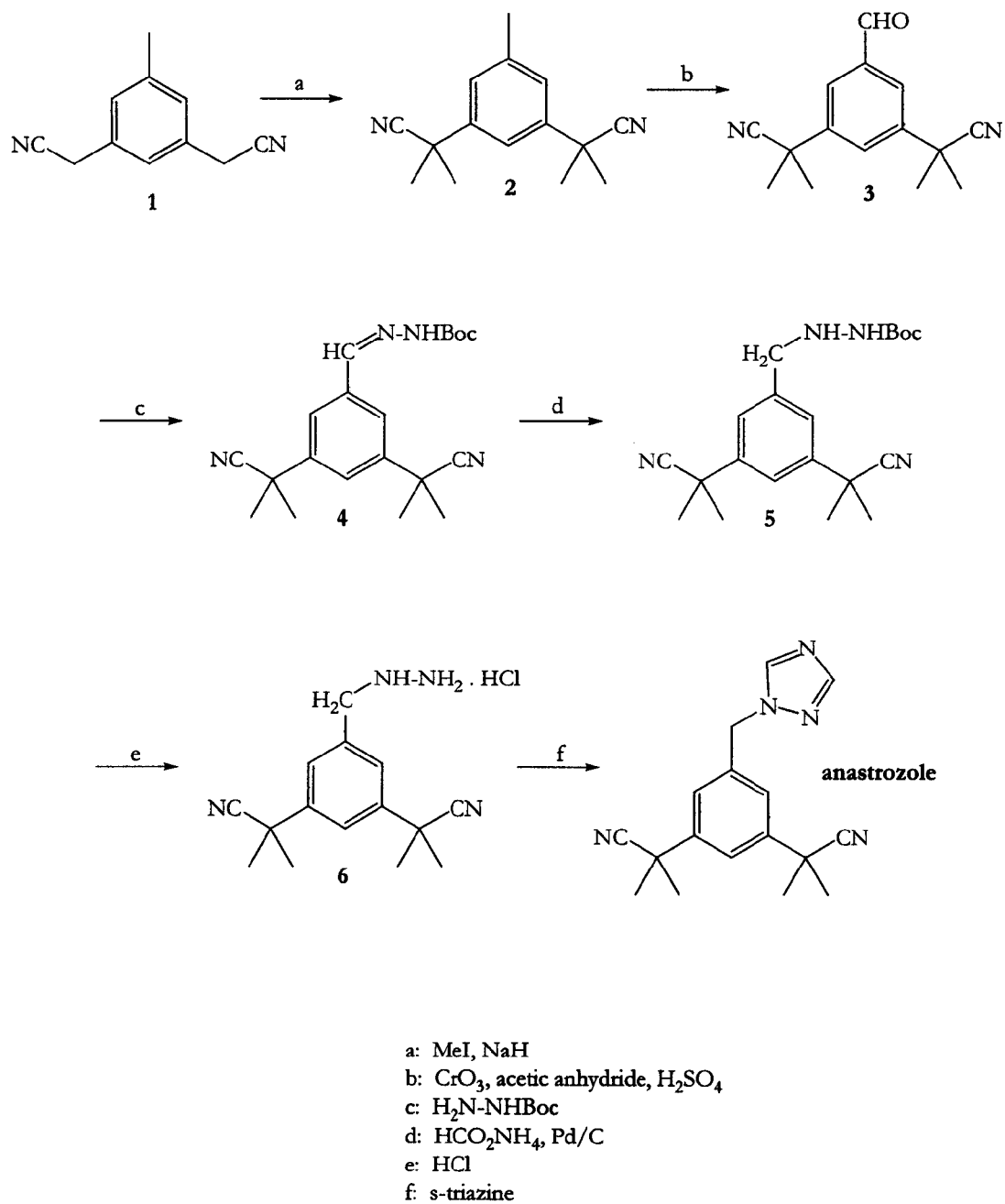
FIG. 2 is a schematic illustration of a preferred process of the present invention.

The preferred embodiment of the first aspect of the invention is illustrated in FIG. 2 wherein R is a Boc group and X is HCl.

The processes outlined in FIGS. 1 and 2 are short and utilise readily available starting materials and reagents. Each step of the process is high yielding and affords products of very high purity.

Therefore a first aspect of the current invention is a process for the preparation of anastrozole comprising one or more of the steps specified in FIG. 1. A preferred embodiment of the first aspect of the invention is the process illustrated in FIG. 2.

A second aspect of the invention is anastrozole and/or its pharmaceutically acceptable salts or derivatives when prepared by a process according to the first aspect of the invention or a pharmaceutical composition comprising anastrozole and/or its pharmaceutically acceptable salts or derivatives when prepared by a process according to the first aspect of the invention.

A third aspect of the invention is novel compound, hydrazone 4a, which is an intermediate in the first aspect of the invention. In compound 4a, group R is a protecting group as specified above. A preferred embodiment of the third aspect of the invention is novel compound 4, wherein R represents a Boc group.

A fourth aspect of the invention is novel compound, hydrazine 5a, which is an intermediate in the first aspect of the invention. In compound 5a, group R is a protecting group as specified above. A preferred embodiment of the fourth aspect of the invention is novel compound 5, wherein R represents a Boc group.

A fifth aspect of the invention is novel compound, hydrazine salt 6a, which is an intermediate in the first aspect of the invention. In compound 6a, group X is an acid as specified above. A preferred embodiment of the fifth aspect of the invention is novel compound 6, wherein X represents HCl.

An example and details of a process of the first aspect of the invention are found in the experimental procedures outlined below. Examples of the third, fourth and fifth aspects of the invention are also included in the experimental procedures below.

EXPERIMENTAL PROCEDURES

Preparation of 2,2'-(5-methyl-1,3-phenylene)di(2-methylpropionitrile) 2

Compound 2, 2,2'-(5-methyl-1,3-phenylene)di(2-methylpropionitrile), can be prepared according to the procedure in example 1 of patent EP 0296749 B1, which is hereby incorporated by reference in its entirety, but in particular in respect of the preparation of 2,2'-(5-methyl-1,3-phenylene)di(2-methylpropionitrile) 2. Yield: 79%. Melting point: 125-127° C.

Conversion of 2,2'-(5-methyl-1,3-phenylene)di(2-methylpropionitrile) 2 to aldehyde 3

Chromium trioxide (10 g, 0.1 mol) was dissolved in acetic anhydride (62.25 ml) at 20-25° C. Solution was stored at −25° C. In a 250 ml 4N flask was charged acetic anhydride (56.6 ml). Tetramethyl compound 2 (11.318 g, 0.05 mol) was added and cooled to −5 to −10° C. Sulfuric acid (11.09 ml) was added at −10 to 0° C. over the period of 30-45 minutes. To this was charged chromium trioxide solution at −10 to 0° C. over the period of 2 hours. The reaction mass was quenched in 679 ml of ice-cold water and extracted with 3×566 ml dichloromethane, washed combined dichloromethane layer successively with 566 ml water, 566 ml 10% $Na_2CO_3$ solution and 566 ml water. Dried over sodium sulfate. Concentration of the DCM to dryness gave 19 g diacetate.

Diacetate (19 g) was dissolved in ethanol (85.5 ml) with slight warming (40° C.). To this was charged water (85.5 ml) and sulfuric acid (3.43 ml). Refluxed for one hour and then reaction mass was quenched in cold water (685 ml). Solid was filtered and washed with cold water followed by hexane. Dried the solid under vacuum at 60° C. to give 9.419 g off-white coloured solid 3. Yield: 78.34%.

Melting point: 138-142° C.

$^1$H NMR ($CDCl_3$): 1.8 (s, 12H, C-9H); 7.886 (t, J=1.8 Hz, 1H, C-2H); 7.95 (d, J=1.8 Hz, 2H, C-4H); 10.07 (s, 1H, C-10H).

$^{13}$C NMR ($CDCl_3$): 29.54 (C-9,9'); 37.84 (C-7,7'); 124.13 (C-8,8'); 126.38 (C-4,6); 128.48 (C-2); 138.07 (C-5); 144.32 (C-1,3); 191.61 (C-10).

IR ($cm^{-1}$, KBr): 2237.46 (CN), 1711.45 (CHO), 1603.93 (Ar).

MS (m/z): 227.5 $(M+H)^+$, 244.5 $(M+NH_4)^+$, 249.5 $(M+Na)^+$, 265.5 $(M+K)^+$, 259.5 $(M+H+MeOH)^+$.

Conversion of Aldehyde 3 to Hydrazone 4

To a mixture of aldehyde 3 (36 g, 0.15 mol) and ethanol (900 ml) was charged mono Boc-protected hydrazine (23.78 g, 0.18 mol). Refluxed for 5 hours. Cooled to 24-26° C. Charged ice-cold water (1000 ml) and filtered the solid and washed with ice-cold water (500 ml) followed by hexane (500 ml). Dried the solid at rotary evaporator at 45° C. to give the off-white coloured solid 4 (41 g). Yield: 77.21%.

Melting point: 188-190° C.

$^1$H NMR ($CDCl_3$): 1.55 (s, 9H, C-13H); 1.76 (s, 12H, C-9H); 7.59 (bs, 1H, C-2H); 7.71 (d, J=1.6 Hz, 2H, C-4H); 7.92 (s, 1H, C-10H); 8.09 (bs, NH).

$^{13}$C NMR ($CDCl_3$): 28.98 (C-13); 29.70 (C-9); 38.0 (C-7); 82.5 (C-12); 123.87 (C-4,6); 124.04 (C-2); 124.69 (C-8); 136.37 (C-5); 143.08 (C-10); 143.59 (C-1,3); 153.21 (C-11).

IR ($cm^{-1}$, KBr): 2238.21 (CN), 1723.5 (C=N), 1701.9 (C=O).

MS (m/z): 241.3 $(M+H)^+$, 258.5 $(M+NH_4)^+$, 263.3 $(M+Na)^+$.

Hydrogenation of Hydrazone 4 to Hydrazine 5

Hydrazone 4 (7 g, 1.98 mmol) was dissolved in methanol (350 ml). Ammonium formate (12.45 g, 19.8 mmol) and 5% palladium on carbon paste (1.4 g, 20% w/w) was added and the reaction mixture refluxed for 4 hours. The hot solution was filtered through a celite bed and the filtrate was concentrated to dryness. The residue was dissolved in ethyl acetate (200 ml) and water (100 ml). The aqueous layer was extracted with ethyl acetate (2×100 ml). The combined organic extracts were dried over sodium sulfate and concentrated under reduced pressure to give 5.63 g of hydrazine 5 as a yellow viscous oil. Yield: 80%.

$^1$H NMR (CDCl$_3$): 1.47 (s, 9H); 1.74 (s, 12H, C-8H); 4.05 (d, J=4.2 Hz, 2H, C-10H); 7.42 (bs, 2H, C-4H); 7.47 (bs, 1H, C-2H).

$^{13}$C NMR (CDCl$_3$): 29.0 (C-13); 29.80 (C-9); 37.9 (C-7); 56.0 (C-10); 81.4 (C-12); 121.6 (C-2); 124.8 (C-8); 125.7 (C-4,6); 140.3 (C-5); 143.1 (C-1,3); 157.3 (C-11).

IR (cm$^{-1}$, CHCl$_3$): 2238.1 (CN), 1713.3 (C=O), 1604.1 (Ar).

MS (m/z): 353.2 (M–H)$^+$.

Conversion of Hydrazine 5 to Hydrazine Hydrochloride 6

Hydrazine 5 (18 g) was dissolved in dichloromethane (180 ml) and concentrated hydrochloric acid (36 ml) was added. The reaction mixture was refluxed for 3 hours. The reaction mixture was cooled, 100 ml water was added and the organic and aqueous layers were separated. The organic layer was washed with 2×100 ml water and the combined aqueous layers were basified to pH 7-8 (pH paper) with sodium carbonate at 10-15° C. The basic aqueous layer was extracted with dichloromethane (3×100 ml). Combined organic extracts were washed with water (100 ml) and dried over sodium sulfate and concentrated under reduced pressure to give hydrazine (9.21 g).

The free base was dissolved in tetrahydrofuran (100 ml), cooled to 0-5° C. and ethereal HCl (35 ml) was added dropwise. White solid precipitated out of solution. The reaction mixture was stirred for 0.5 hours and filtered. The residue was washed with tetrahydrofuran (15 ml) and dried on the rotavapor to give the hydrazine hydrochloride 6 as a white solid (7.81 g). Yield: 52.82% (over two steps).

$^1$H NMR (CD$_3$OD): 1.81 (s, 12H, C-9H); 4.25 (s, 2H, C-10H); 7.65 (d, J=1.75 Hz, 2H, C-4H); 7.71 (d, J=1.75 Hz, 1H, C-2H).

MS (m/z): 357.3 (M+H)$^+$.

Conversion of Hydrazine Hydrochloride 6 to Anastrozole

Hydrazine hydrochloride 6 (7.71 g) and s-triazine (3.2 g) was refluxed in ethanol (77.1 ml) for 2 hours. The reaction mixture was concentrated to dryness, dissolved in dichloromethane (77 ml) and washed with water (77 ml). The aqueous layer was extracted with dichloromethane (2×40 ml) and the combined organic extracts were washed with water (2×50 ml). The organic layer was dried over sodium sulfate, concentrated to dryness under reduced pressure to give the product as a light-yellow oil (6.57 g).

The oil was stirred with 5% ethyl acetate in hexane (66 ml) for 30 minutes. White solid obtained was filtered, washed with 5% ethyl acetate in hexane (34 ml) and dried under reduced pressure at 15 mbar/45° C. to give anastrozole as a white solid (5.6 g). Yield: 72.49%.

Melting point: 79-80° C.

$^1$H NMR (CDCl$_3$): 1.72 (s, 12H, C-9H); 5.4 (s, 2H, C-10H); 7.33 (d, J=1.5 Hz, 2H, C-4H); 7.54 (d, J=1.5 Hz, 1H, C-2H); 8.00 (s, 1H, C-11H or C-12H); 8.15 (s, 1H, C-12H or C-11H).

MS (m/z): 294.3 (M+H)$^+$.

Purity: >99.5% measured by HPLC.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A process for the preparation of anastrozole, comprising two or more of the steps:

(a) methylation of diacetonitrile 1 to yield diacetonitrile 2,

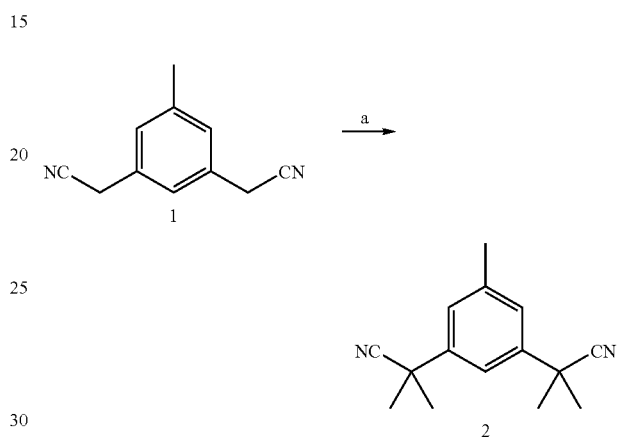

(b) oxidation of diacetonitrile 2 to yield aldehyde 3,

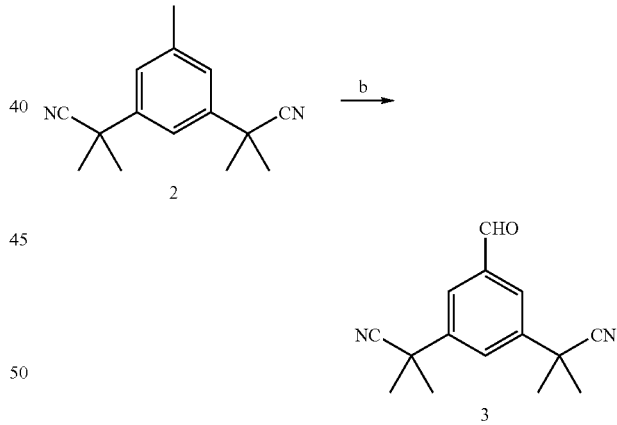

(c) conversion of aldehyde 3 to yield hydrazone 4a,

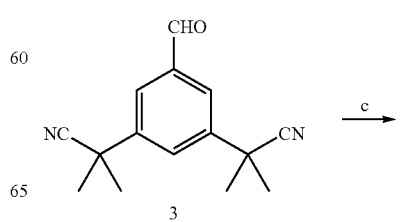

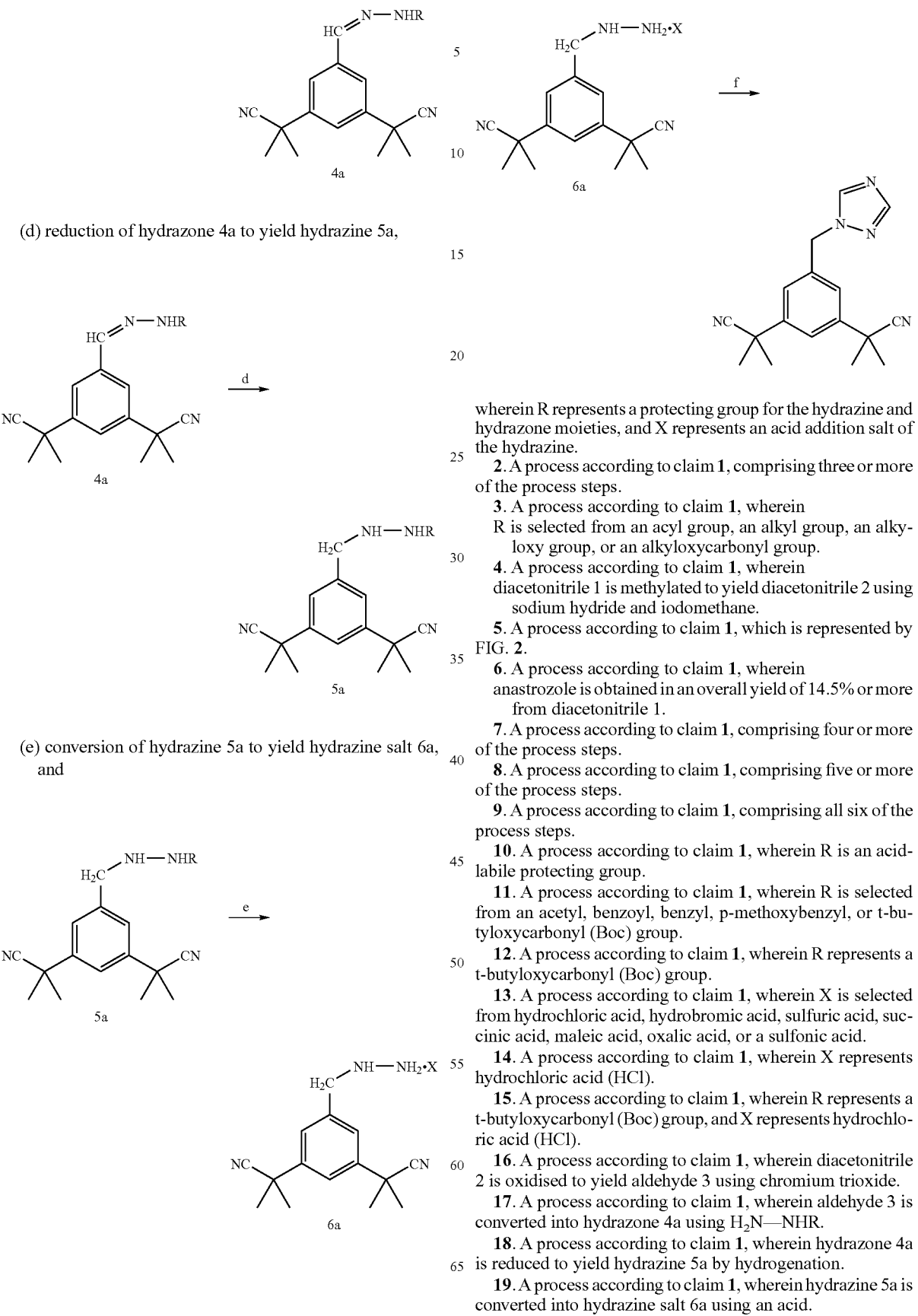

(d) reduction of hydrazone 4a to yield hydrazine 5a, (e) conversion of hydrazine 5a to yield hydrazine salt 6a, and (f) conversion of hydrazine salt 6a to yield anastrozole, wherein R represents a protecting group for the hydrazine and hydrazone moieties, and X represents an acid addition salt of the hydrazine.

2. A process according to claim 1, comprising three or more of the process steps.

3. A process according to claim 1, wherein
R is selected from an acyl group, an alkyl group, an alkyloxy group, or an alkyloxycarbonyl group.

4. A process according to claim 1, wherein
diacetonitrile 1 is methylated to yield diacetonitrile 2 using sodium hydride and iodomethane.

5. A process according to claim 1, which is represented by FIG. 2.

6. A process according to claim 1, wherein
anastrozole is obtained in an overall yield of 14.5% or more from diacetonitrile 1.

7. A process according to claim 1, comprising four or more of the process steps.

8. A process according to claim 1, comprising five or more of the process steps.

9. A process according to claim 1, comprising all six of the process steps.

10. A process according to claim 1, wherein R is an acid-labile protecting group.

11. A process according to claim 1, wherein R is selected from an acetyl, benzoyl, benzyl, p-methoxybenzyl, or t-butyloxycarbonyl (Boc) group.

12. A process according to claim 1, wherein R represents a t-butyloxycarbonyl (Boc) group.

13. A process according to claim 1, wherein X is selected from hydrochloric acid, hydrobromic acid, sulfuric acid, succinic acid, maleic acid, oxalic acid, or a sulfonic acid.

14. A process according to claim 1, wherein X represents hydrochloric acid (HCl).

15. A process according to claim 1, wherein R represents a t-butyloxycarbonyl (Boc) group, and X represents hydrochloric acid (HCl).

16. A process according to claim 1, wherein diacetonitrile 2 is oxidised to yield aldehyde 3 using chromium trioxide.

17. A process according to claim 1, wherein aldehyde 3 is converted into hydrazone 4a using $H_2N$—NHR.

18. A process according to claim 1, wherein hydrazone 4a is reduced to yield hydrazine 5a by hydrogenation.

19. A process according to claim 1, wherein hydrazine 5a is converted into hydrazine salt 6a using an acid.

20. A process according to claim 1, wherein hydrazine salt 6a is converted into anastrozole using s-triazine.

21. A process according to claim 1, wherein anastrozole is obtained in batches of 5.6 g or more.

22. A process according to claim 1, wherein anastrozole is obtained on an industrial scale.

23. A process according to claim 1, wherein anastrozole is obtained in batches of 0.5 kg or more.

24. A process according to claim 1, wherein anastrozole is obtained in batches of 5 kg or more.

25. A process according to claim 1, wherein anastrozole is obtained in batches of 25 kg or more.

26. A process according to claim 1, wherein the anastrozole obtained is more than 98% pure.

27. A process according to claim 1, wherein the anastrozole obtained is more than 99.5% pure.

28. A process according to claim 1, wherein the anastrozole obtained is more than 99.9% pure.

* * * * *